United States Patent [19]
Chisum

[11] Patent Number: 5,874,045
[45] Date of Patent: Feb. 23, 1999

[54] FORENSIC SAMPLER

[76] Inventor: William J. Chisum, 9312 Quesnel Dr., Elk Grove, Calif. 95758-1044

[21] Appl. No.: 40,715

[22] Filed: Mar. 18, 1998

Related U.S. Application Data

[62] Division of Ser. No. 734,781, Oct. 15, 1996, Pat. No. 5,780,305.

[51] Int. Cl.⁶ ........................................................ G01N 1/00
[52] U.S. Cl. ........................... 422/58; 422/100; 422/102; 422/103; 422/104; 436/174; 436/180; 206/363; 435/30; 604/1
[58] Field of Search .............................. 422/58, 101, 100, 422/102, 103, 104; 436/174, 180; 604/1; 206/363; 435/30

[56] References Cited

U.S. PATENT DOCUMENTS

| | | | |
|---|---|---|---|
| 2,835,246 | 5/1958 | Boettger | 128/2 |
| 3,513,830 | 5/1970 | Kalayjian | 128/2 |
| 4,136,680 | 1/1979 | Southworth | 128/213 |
| 4,457,313 | 7/1984 | Alter | 128/759 |
| 4,749,655 | 6/1988 | Monthony et al. | 435/295 |
| 4,952,204 | 8/1990 | Korteweg | 604/1 |
| 5,025,920 | 6/1991 | Walsh et al. | 206/223 |
| 5,112,152 | 5/1992 | McBride | 401/132 |
| 5,163,441 | 11/1992 | Monthony et al. | 128/759 |
| 5,511,654 | 4/1996 | De La Rocha | 206/15.3 |

*Primary Examiner*—Harold Y. Pyon
*Attorney, Agent, or Firm*—Medlen & Carroll, LLP

[57] ABSTRACT

The invention generally relates to an easy-to-use device for the safe and secure transport of samples and specimens from the field to the laboratory. The invention is particularly suited for use with forensic samples, as it facilitates the drying of the sample, while protecting the sample from the environment and protecting the environment from contamination with the sample.

4 Claims, 4 Drawing Sheets

FORENSIC SAMPLER

This is a divisional of application Ser. No. 08/734,781, filed Oct. 15, 1996 now U.S. Pat. No. 5,780,305.

FIELD OF THE INVENTION

The invention generally relates to an easy-to-use device for the safe and secure transport of samples and specimens from the field to the laboratory. The invention is particularly suited for use with forensic samples.

BACKGROUND

Crime scene evidence such as that collected on sample swabs often provides critical information necessary for identification of suspects and the determination of guilt or innocence of accused individuals at trial. Often, the evidence is in the form of body fluids such as blood, semen, saliva, urine, etc. Care must be taken to ensure that the sample collected is: representative of the evidence present at the crime scene (i.e., it is related to the crime); labelled properly and appropriately (i.e., with the case number, type of specimen, etc.); and that the sample is transported properly and in a timely manner to the crime laboratory. In addition, care must be taken to avoid contamination of the sample with extraneous material. This is particularly important in cases where DNA testing will be conducted on the sample.

Decay of biological samples by bacteria and other microorganisms, as well as other environmental conditions (e.g., heat or high temperatures) must be avoided in order to ensure that the collected sample will provide the necessarily reliable answers upon analysis. For example, it is known that DNA is rapidly degraded in moist, warm conditions, with most of the DNA in tissue specimens degrading within days or even hours. However, DNA is extremely stable under certain environmental conditions. Acceptable DNA analyses may be performed on dried blood and semen stains collected many weeks prior to the analysis (See e.g., S. Easteal el aL, *DNA Profiling Principles, Pitfalls and Potential*, Harwood Academic Publishers, Philadelphia, at p. 68, [1991]). In addition to DNA analyses, other types of biological sample analysis is routinely conducted on dried samples, including serological (i.e., electrophoretic or immunologic) methods to identify antigens and/or proteins present in the samples. Thus, rapid and thorough drying of samples is routinely encouraged in the collection and handling of forensic samples (See e.g., S. Easteal el al., supra, at pages 141–142; and S. H. James, "The Documentation, Collection, and Evaluation of Bloodstain Evidence," in W. G. Eckert and S. H. James, *Interpretation of Bloodstain Evidence at Crime Scenes*, Elsevier, New York, at pages 87–113 [1989]).

However, it is often very cumbersome to dry samples on site at crime scenes. The use of forced air (e.g., fans, or cold hair dryers), or air drying the samples, presents problems. For example, fans and hair dryers must be included in the crime laboratory's equipment pack, and they usually require an electrical source in order to work. In addition, it is important not to use heat to dry the samples, as the high temperatures may degrade the samples. Furthermore, if trace evidence is involved, fans are not recommended, especially if more than one item is being dried at the same time, as cross-contamination must be avoided (See, J. M. Rynearson and W. J. Chisum, *Evidence and Crime Scene Reconstruction*, National Crime Investigation and Training, pages 57–62 [1983]). Thus, although forced air methods may provide advantages in terms of speed, other considerations, such as the availability of the needed equipment, and the risk of cross-contamination must be kept in mind. Although air drying avoids the need for equipment such as fans and hair dryers, it is often impractical, as time is required for the sample to dry adequately. In addition, if the sample is left exposed to the air without any type of protection, the chances of sample contamination increase. For example, a swab containing a blood sample that is left to dry on a countertop may become contaminated while other evidence from the crime scene is being collected, and perhaps even placed in close proximity with the drying swab. These factors are important in court as such opportunities for contamination may provide the doubt necessary for an acquittal of the suspect in the case.

Although drying of samples at the crime scene is preferred, it may not be accomplished. This leads to problems associated with the transport of wet samples to the crime laboratory. For example, criminalists and crime scene technicians often place inadequately dried samples into paper envelopes or bags, or wrap them in index cards for transport (See e.g., U.S. Pat. No. 5,025,920, to Walsh et al.). The paper allows the sample to leak through the envelope or bag, contaminating the environment surrounding the sample, and reducing the volume of the sample available for testing. If many samples are placed close together, the potential for cross-contamination of the samples is present. Thus, the reliability of all of the samples in the collection may become questionable, a factor the defense attorney will highlight during the trial of the accused suspect.

Double bagging of the sample by use of a rolled up index card to protect the sample, and then placing the card in a second evidence container, such as an envelope, may help avoid the problems of contamination of the environment with wet samples. However, time must be taken to carefully staple the moist swab to the index card, label the card in a location where the sample will not contact the ink or pencil markings (i.e., to prevent the sample from rendering the label unreadable), roll the card, and then staple the card in a manner such that the card completely surrounds the sample except at the end (i.e., the card resembles the shape of a bullhorn, with the sample stapled to the inside of the horn). Another problem is presented by the cards in that they are easily crushed during transport of the sample. In addition, because the wet sample is in contact with the card, the sample may be allowed to leak through the card, leading to the same concerns as discussed above. Furthermore, this system is not designed to facilitate the drying of the sample at a rapid rate.

Plastic transport bags do not provide the answer to the prevention of sample contamination. Although the plastic bag will help to prevent contamination of the sample due to materials falling or dropping on to the sample. Placing a wet sample in a plastic bag creates an ideal environment for bacterial and fungal growth, as the moistness is retained within the bag and often the temperature is optimal for microbial growth. This leads to the degradation of the sample, again decreasing its reliability and value.

Although the use of medical sampling and transport devices might, at first appear to provide the answer, the medical situation is diametrically opposed to that of forensics. Swabs for medical testing and analysis are often collected and transported in plastic or other containers (See e.g., U.S. Pat. No. 4,749,655, to Monthony, U.S. Pat. No. 5,163,441, to Monthony, U.S. Pat. No. 4,136,680, to Southworth, U.S. Pat. No. 2,835,246 to Boetter, U.S. Pat. No. 3,513,830, to Kalayjian, U.S. Pat. No. 4,457,313, to Alter, etc.). However, these devices and methods are intended to protect the microorganisms present on the swab, while preventing contamination of the sample and environment. Thus, the swabs are often placed into media which protect the microorganisms from drying or other environmental stresses. Indeed, specialized transport media have been developed for such uses (See e.g., R. M. Atlas, *Handbook of Microbiological Media*, CRC Press, Boca Raton, pages 67–68, 179, 190, 193, 510, 653–654, 764, 836, 854–855, 920–922, 978, and 985 [1993]).

What is needed in the art is a means to transport forensic samples to the laboratory in a manner that encourages the sample to dry, as well as protect it and the environment from contamination, and avoid the loss of sample to leakage or other factors.

SUMMARY OF THE INVENTION

The present invention is directed to methods and devices for the drying and transport of forensic samples. In particular, the present invention provides means to effectively dry samples collected on swabs in a short time period, while protecting both the sample and its surrounding environment. After a sample is collected with the swab, the sampling head may be drawn into a special shield device. The swab is positioned within the approximate center of the shield and is prevented from touching the shield.

More specifically, the present invention contemplates a sample collection and transport device, comprising a) a sample collection means including a shaft having distal and proximal ends and a sampling head mounted on the proximal end of the shaft; and b) a shield having a collar for slidingly engaging the shaft of the sample collection means, the shield having a shape and size sufficiently large to surround the sampling head without substantially touching the sampling head when the sampling head is drawn into the shield. In some embodiments, the shield of the sample collection and transport device is perforated, whereas it is a solid material in other embodiments. The shield of the sample collection and transport device may be comprised of a variety of materials; in some embodiments it is composed substantially of plastic. In certain embodiments of the present invention, the sampling head of the collection means is an absorbent. In still further embodiments, the collar of the sample collection and transport device is a guiding hub.

The present invention also contemplates various methods for collecting evidence samples. To illustrate, the present invention contemplates a method for collecting evidence samples using a sample collection means having a shaft and a sampling head mounted on a proximal end of the shaft and a shield slidingly mounted on a distal end of the shaft, comprising the steps of a) exposing the sampling head to a sample, thereby providing a collected sample; and b) drawing the sampling head containing the collected sample into the shield by pulling the distal end of the shaft away from the shield, thereby providing an evidence sample. In particular embodiments, the shield is constructed of a solid material, whereas the shield is perforated in other embodiments. Moreover, in some embodiments the shield further comprises a collar; in other embodiments, the shield further comprises a guiding hub. In still further embodiments, the method of collecting evidence samples also comprises the step of allowing the collected sample to dry. The method of collecting evidence samples further comprises the step of placing the evidence sample within a transport apparatus in additional embodiments. When the evidence sample is placed within a transport apparatus, the present invention contemplates transporting the evidence sample in certain embodiments.

The present invention contemplates alternative methods for collecting evidence samples. One such method involves collecting evidence samples using a sample collection means having a shaft and a sampling head mounted on a proximal end of the shaft and a shield having a guiding hub wherein the shield is slidingly mounted on a distal end of the shaft, comprising the steps of a) exposing the sampling head to a sample to provide a collected sample; and b) drawing the sampling head containing the collected sample through the guiding hub of the shield by pulling the distal end of the shaft away from the shield, thereby providing an evidence sample. In one embodiment, the shield is perforated. In particular embodiments, the method further comprises the step of allowing the collected sample to dry. Additionally, some embodiments further comprise the step of placing the evidence sample within a transport apparatus. When the evidence sample is placed within a transport apparatus, the present invention contemplates transporting the evidence sample in certain embodiments.

DESCRIPTION OF THE INVENTION

Figure 1A:
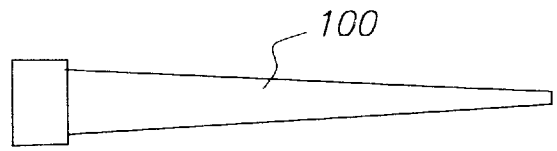
FIGS. 1A–E depict one embodiment of the present invention, in which the shield of the sample collection and transport device is comprised of plastic.

The present invention is intended and designed to eliminate problems commonly encountered in the collection and transport of biological evidence from crime scenes to the laboratory. In particular, the present invention avoids problems associated with samples that are packaged and transported wet. Unlike the rolled index cards, paper envelopes, or bags, in use by some laboratories, the present invention prevents the swab from touching the sides of the transport container (i.e., the shield). Thus, unlike paper envelopes or bags, the sample does not leak through the transport container, thereby preventing contamination of the environment and maintaining the volume of sample collected. Loss of the sample due to leakage or seeping through the transport container is an important factor to be avoided, especially in cases where a limited sample size is available. The present invention prevents this problem as the sample is prevented from touching the shield.

Thus, the present invention is directed toward a specialized swab and transport apparatus for collection of specimens used in forensic analyses. After a sample is collected with the swab, the sampling head can be drawn into a special shield device. In one preferred embodiment, the shield device is of solid material, such that air is permitted to enter the shield at one end of the device (i.e., the distal end of the shield).

In an alternative embodiment, openings such as perforations, or other means to vent the interior of the shield are present in the shield to allow ready air circulation around the absorbent tip of the swab (i.e., the "sampling head"), so that the specimen dries on the swab. The swab is positioned within the approximate center of the shield and is prevented from touching the shield. In this manner, the sample present on the tip of the swab dries quickly and is protected from the environment, while also protecting the environment from the sample.

Unlike the present invention, commonly used swab and transport systems are designed so that the swabs are kept moist in order to maintain the viability of microorganisms present on the swab. While Monthony et al. (U.S. Pat. No. 5,163,441) teach the use of a dry polyurethane swab to collect and transport samples used for antigen detection, this patent, as well as other patents such as U.S. Pat. No. 4,749,655, to Monthony, U.S. Pat. No. 4,136,680, to Southworth, U.S. Pat. No. 2,835,246 to Boetter, U.S. Pat. No. 3,513,830, to Kalayjian, and U.S. Pat. No. 4,457,313, to Alter, disclose transport systems in which the transport system is a key feature in the prevention of microbial contamination of laboratory or medical personnel and the environment. These devices are designed in a manner that the sample is tightly sealed within the transport container, thereby preventing any contact between the sample and the outside air. In contrast, the present invention facilitates the contact of air with the sample, in order to permit rapid drying of the sample.

The Walsh et al Patent (U.S. Pat. No. 5,025,920) teaches that evidence samples should be dried in order to prevent deterioration. However, unlike the present invention, Walsh et al. teach the use of porous bags to transport the specimens from crime scenes to the laboratory. Walsh et al. indicate that although the use of plastic bags helps to preventing contamination, the bags retard sample drying (See, Walsh et al., col. 1, lines 35–39). By using a porous bag, the sample in Walsh's invention is permitted to dry more easily than in plastic bags. However, Walsh et al do not avoid the problems associated with transport of a wet evidence bag, such as contamination of other surfaces with sample blood or other fluids that have soaked through the bag, as well as loss of some of the sample. Likewise, Walsh et al. do not teach or mention the use of a venting or hole-containing shield to allow sample drying and prevent wetting of the transport container.

The present invention also contemplates an area suitable for identification of the sample. For example, the shield may comprise a labelling area, in which the case number, victim, suspect, and/or other information may be written. This labelling area may comprise an etched or non-etched portion of the shield. As the sample is dried rapidly and is not permitted to contact the shield, the chances of the sample rendering the label illegible are minimized.

Thus, the present invention provides a heretofore unavailable methods for the rapid drying of swabs, as well as methods for the safe and secure transport of samples to the crime laboratory, during which the integrity of the sample and the surrounding environment is maintained.

Definitions:

To facilitate further understanding of the invention, a number of terms are defined below:

The terms "sample" and "specimen" in the present specification and claims are used in their broadest sense. On one hand, they are meant to include a specimen or culture. On the other hand, they are meant to include both biological and environmental samples. These terms encompasses all types of samples obtained from humans and other animals, including but not limited to, body fluids such as blood, semen, saliva, sputum, fecal matter, urine, and cerebrospinal fluid (CSF), as well as solid tissue. These terms also refer to swabs and other sampling devices which are commonly used to obtain samples for culture of microorganisms or for collection of evidence samples for forensic analyses.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention. However, it is intended that all of the samples used with the present invention be dried.

As used herein, the term "swab" encompasses any material useful in the collection of samples. Commonly, swabs are comprised of "sampling heads" and "shafts" or "handles."

As used herein, the term "sampling head" refers to the portion of a swab that is used to collect the sample of interest, upon which the sample is incorporated or located. Sampling heads are often constructed of absorbent and/or adsorbent materials, such that the sample is adsorbed into the material of the sampling head or is stuck to the sampling head by other forces. The present invention contemplates sampling heads comprised of materials, including but not limited to, cotton, polyester, rayon, teflon, and other synthetic and natural materials.

As used herein, the "shaft" encompasses any materials useful as a shaft or handle for the collection of samples on or in swabs. Thus, the present invention contemplates the use of materials including, but not limited to wood, plastics, resins, various synthetic materials, paper, etc. Indeed, the shaft may be of any material to which a sampling head may be attached and used for the collection of samples. The shaft of the swab may be described as having both distal and proximal ends. The proximal end of the shaft is the portion of the swab that is closest to the shield when the swab is located within the shield device. The distal end of the shaft is the portion of the swab that extends beyond the guiding hub of the shield (i.e., it is not located within the portion of the shield that protects the sampling head from the environment). It is contemplated that the distal end of the shaft may be cut or clipped, in situations in which it is desirable to have a shorter length of shaft extending from the shield.

As used herein, the term "perforation" refers to any means by which air is allowed to pass through the shield to circulate around the sampling head and sample, when the swab is located within the shield. The term is used in reference to any opening in the shield by which air is allowed to pass into the shield. Thus, it is intended that the term encompass round, oval, square, octagonal, hexagonal, triangular, or any other shape of openings, including slits (i.e., one dimension, such as the length of the structure is bigger than the other dimension [such as the width]), or the mesh of a meshwork, or any other structure that allows air to circulate around the sample present on the sample head.

As used herein, the term "shield" encompasses any structure which partially or completely surrounds the sample present on or within the sampling head, but is itself not in direct contact with the sampling head. Thus, the present invention contemplates the use of materials including, but not limited to, plastics, polymers, glass, paper, cardstock, or any other material that permits the swab to be protected but without contact with any surface. It is also intended that the shield be of any shape or design, so long as the size of the shield is such that the sample is protected from contact with the environment outside the shield and the inner surface of the shield, while air is permitted to circulate around the swab to dry the sample present on the tip of the swab. Thus, shapes such as tapered cylinders, tapered cones, rounded tubes, hexagonal, octagonal, and other shapes are contemplated as being useful as the shield. A few representative shapes are schematically drawn in FIGS. 5A–5D. Shields may include such elements as "rims" and "guiding hubs." The rim of the shield may also be described as the "distal" end of the shield, while the area of the shield closest to the hub may be described as the "proximal" end of the shield.

Figure 5A:
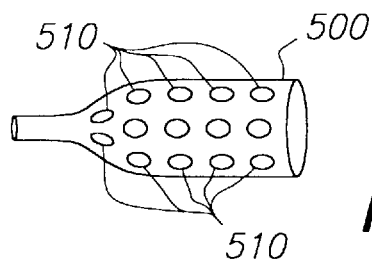
FIGS. 5A–D depict four alternative shapes of the shield of the sample collection and transport device of the present invention.
Figure 5B:
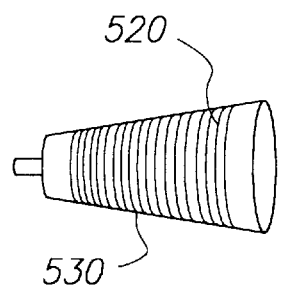
Figure 5C:
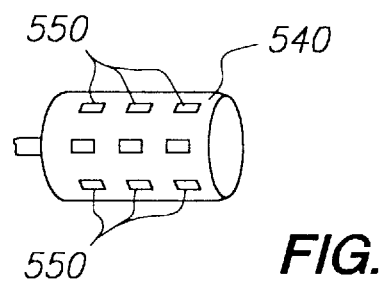
Figure 5D:
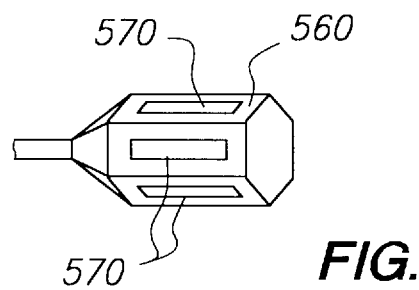

FIG. 5A–5D a schematic representation of four alternative embodiments of the shield. FIG. 5A shows the shield as a tapered cylinder (500), with rounded openings (510); FIG. 5B, shows the shield as a tapered cone (520), with a meshwork (530) to permit air circulation around the swab and sampling head; FIG. 5C shows the shield as a rounded cylinder (540) with square-shaped openings (550); and FIG. 5D shows the shield as a hexagon or octagon (560), with slits (570) to permit air circulation around the swab and sampling head.

It is intended that any of these shield designs or combinations thereof (e.g., a tapered cylinder with slits, or a rounded cylinder with round or oval openings) be encompassed by the present invention. It is also not intended that the present invention be limited to any particular number, size, and shape of the perforations, openings, or openings or location on the shield. Indeed, it is intended that any design which protects the sample from the environment, prevents the contact of the sampling head of the swab with the transport container, and readily permits drying of the sample be encompassed by the present invention. However, it is not intended that the shield of the present invention be limited to these particular shapes. The shield of the present invention may also include such structures as "guiding hubs," "collars," and the like.

Figure 4:
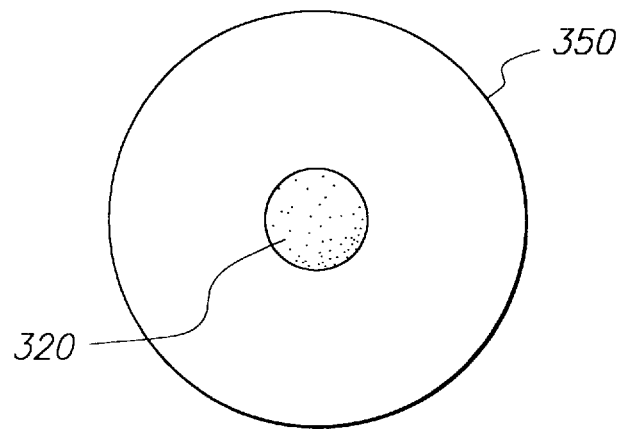
FIG. 4 depicts a cross-sectional view of one embodiment of the present invention taken along the R—R line in FIG. 3C.

As used herein, the terms "guiding hub" and "collar" refer to aspects of the shield which help position the swab within the shield. For example, the cut tip of a pipet through which the shaft of the swab is placed can be considered a "collar" or "guiding hub." In addition, embodiments, such as those illustrated in FIG. 4 include a "guiding hub," through which the swab is placed in order to position the sampling head in the approximate center of the shield. In the embodiment of FIG. 4, the guiding hub does not function as a part of the shield, unlike the embodiments depicted in FIGS. 1A–3D. Thus, it is contemplated that the collar or guiding hub be a part of the shield that protects the swab from the environment, or it may be designed to simply properly position the swab within the shield.

As the characteristics of the swab and/or sampling head size may vary, largely dependent upon the sample to be collected (i.e., a large sampling head may be used to collect large samples, while a small sampling head would be more suitable for small samples), it is intended that the shield size be modified according to the size of the sampling head. For example, a large shield would be unnecessary and cumbersome for use with a small sampling head. However, a large shield would be required with sampling heads of large size. It is also contemplated that the shaft size may vary, depending upon the circumstances under which the swab is used. In some instances, it may be desirable to use a shaft of a small diameter, while in other cases, a large diameter shaft is required. In a like manner, it is intended that the shaft be of any length suitable for the purpose of collecting and transporting samples. Thus, it is intended that the present invention be modified to accommodate any size of swab.

As used herein, "dried" refers to samples and sampling heads which are dry. For example, it is intended that the sample collected on the sampling head be dried sufficiently such that moisture does not drip from the sampling head. It is contemplated that any degree of sample dryness be encompassed by the present invention. However, it is preferred that the sample be adequately dried so that sample degradation is avoided.

EXAMPLES

The following examples are provided in order to demonstrate and further illustrate certain preferred embodiments and aspects of the present invention and are not to be construed as limiting the scope thereof.

In the examples which follow, the following abbreviations apply: ml (milliliters); cm (centimeters); mm (millimeters); μm (micrometers); nm (nanometers); Eppendorf (Eppendorf North America, Inc., Madison, Wis.); and Fisher (Fisher Scientific, Pittsburg, Pa.).

EXAMPLE 1

Pipet Tip Shield

In this Example, a plastic pipet tip was used to provide a shield for evidence samples collected on swabs. One end of a 1 ml pipet tip (100), such as those commercially available from various suppliers such as Eppendorf (See e.g., Fisher Catalog No. 21-377-1C and 21-375E), was cut to form a collar (160), and the distal end (150) of a shaft (110) of a commercially available swab (e.g., Fisher) (120) was inserted into the pipet tip. The sampling head (140) of the swab was used to collect the sample. Then, the swab was manipulated by pushing the distal end (150) of the shaft through the collar (160), in a manner so as to locate the sampling head (140) within the approximate center of the shield. The sample was allowed to dry within the shield, and transported to the laboratory. The shield containing the swab may be placed within another evidence collection container (e.g., an envelope or bag), in order to provide additional protection. However, it is preferred that the sampling head be allowed to dry prior to placing the shield within another container.

Figure 1B:
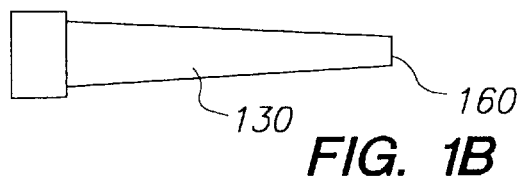
Figure 1C:
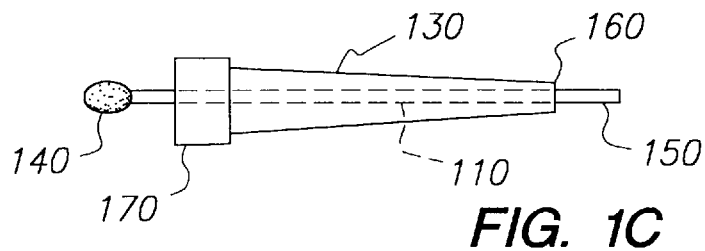
Figure 1D:
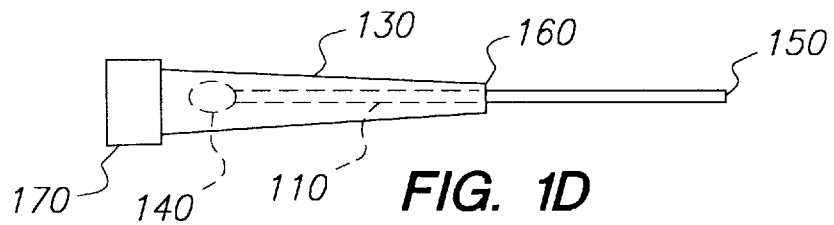
Figure 1E:
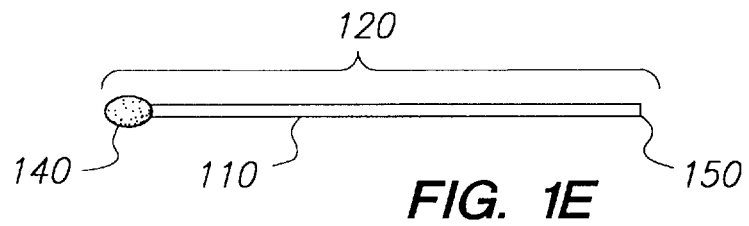

FIG. 1A–1E show schematic illustrations of this embodiment of the present invention. FIG. 1A shows the pipet tip (100) prior to cutting. FIG. 1B shows the pipet tip after cutting to form the collar (160) of the shield (130). FIG. 1C shows the shield with the swab (110) inserted into the shield (130). In this Figure, the sampling head (140) is extended beyond the shield (i.e., the sampling head is exposed to the environment). This position is obtained by pushing the distal end (150) of the swab shaft (110) through the collar (160) and toward the shield, in a manner that the sampling head (140) is extended outside the shield (i.e., the sampling head is positioned beyond the rim [170] of the shield). In this position, the sampling head is available for collection of evidence; the shaft and shield may be used as support during sample collection. FIG. 1D shows the position of the swab when the sampling head is located within the shield ready to be dried and transported to the crime laboratory. FIG. 1E shows the swab (120) in isolation, with the sampling head (140) and distal end (150) of the shaft (110) labelled. In this Example, the sample was identified by marking the shield with an indelible marking pen.

EXAMPLE 2

Plastic Shield

Figure 2A:
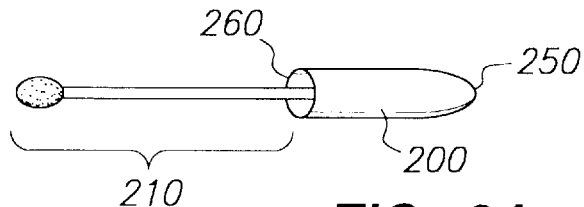
FIGS. 2A–C depict an alternative embodiment of the present invention, in which the shield of the sample collection and transport device is comprised of plastic.
Figure 2B:
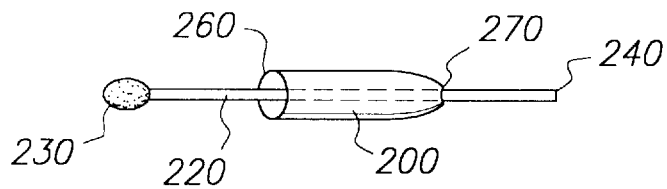
Figure 2C:
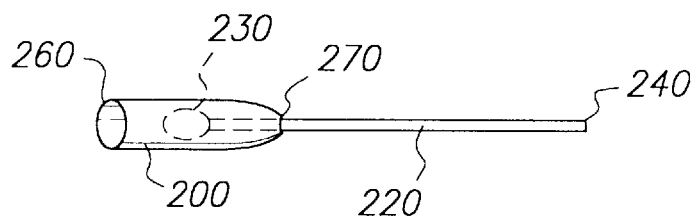

In this Example, a plastic shield was developed for use in the present invention. A plastic tube with one closed end (250) and one open end (260), which contained a swab attached to the closed end, was used in this Example, as shown in FIG. 2. These swabs are commonly used for collection of samples for microbiological analysis and are commercially available from Fisher (e.g., the Precision Culture C.A.T.S. swab system; See e.g., Fisher Catalog No. 14-905-1). However, unlike their use in the medical laboratory, in this Example, the closed end of the tube (250) was cut to form a collar (270), so that the swab was free to be manipulated within the tube. This embodiment is schematically illustrated in FIGS. 2A–2C.

In FIG. 2A, the tube (200) and swab (210) device is shown, with the open end (260) and closed end (250) of the tube indicated. In FIG. 2B, the sampling head (230) of the swab is shown extending beyond the open end (260) of the tube (now a shield [200]); the distal end of the shaft (240) is labelled as well. Also, as shown in FIG. 2B, the sampling head of the swab (230) is in position to collect a sample. After the sample was collected, the distal end of the swab (240) was pulled in a manner which placed the sampling head (230) in the approximate center of the shield (200).

In FIG. 2C, the sampling head (230) is located within the shield (200), ready for transport to the crime laboratory. In this Example, the sample was identified by marking the plastic of the shield with an indelible marking pen.

EXAMPLE 3

Plastic Shield With Perforations

Figure 3A:
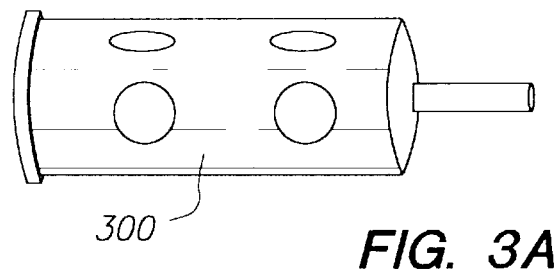
FIGS. 3A–D depict another embodiment of the present invention, in which the shield of the sample collection and transport device is comprised of perforated plastic.
Figure 3B:
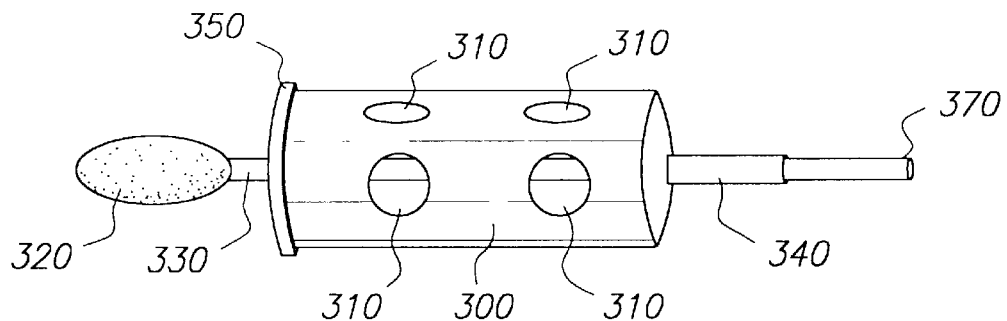
Figure 3C:
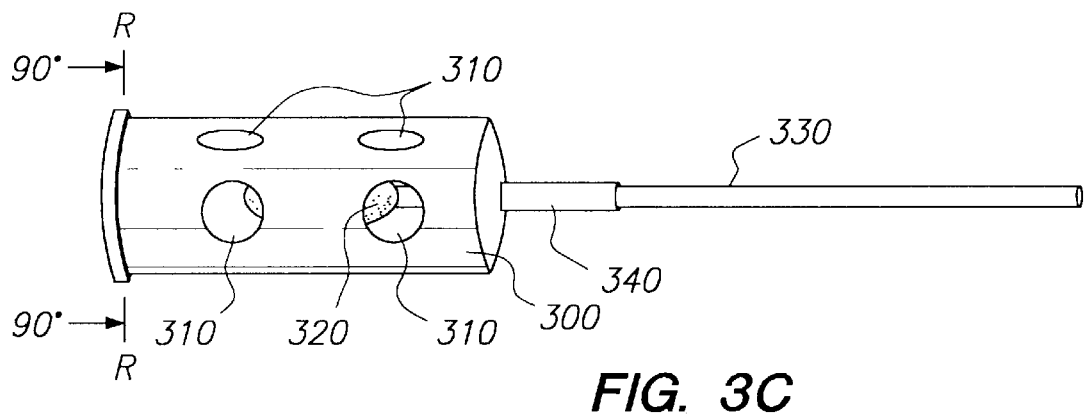
Figure 3D:
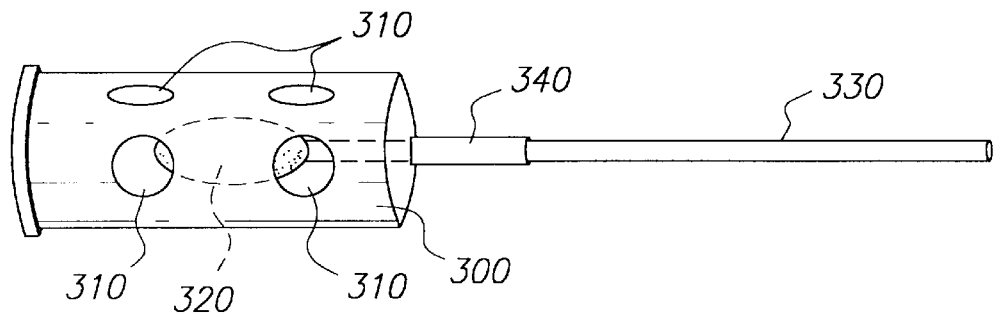

In this Example, a plastic shield was created which included perforations in the form of openings. In this embodiment, the shield facilitated drying of the sample, while protecting the environment from contamination by the sample, and protecting the sample from the environment and the inner surface of the shield. This shield is schematically shown in FIGS. 3A–3D. In this Figure, the shield (300) was created by molding plastic into a tube and either punching openings (310) in the plastic or by using a mold which created openings (310) during the production of the shield. In FIG. 3A, the shield (300) is shown in isolation. In FIG. 3B, the shield is shown with a swab (330) positioned within the shield so that the sampling head (320) extends beyond the distal end of the shield (i.e., the sampling head extends past the rim [350] of the shield). In this position, the sampling head of the swab (320) is available for sample collection, and a large proportion of the shaft of the swab (330) is positioned within the shield. It can be seen that in this Figure, the shaft of the swab is placed within a guiding hub (340) present at the proximal end of the shield. However, in some cases, it is desirable to first collect the sample with the sampling head (320) of the swab, and then place the shaft of the swab (330) within the guiding hub of the shield as shown in FIGS. 3A–3D. This is accomplished by pushing the distal end of the shaft (370) through the shield (300) and the guiding hub (340). Once the shaft is in position, the swab is ready to be drawn into position such that the sampling head (320) is located within the approximate center of the shield (300). This may be accomplished by pulling the distal end of the shaft (370) until the sampling head is positioned within the approximate center of the shield. This is shown in FIG. 3C. The guiding hub (340) functions to hold the shaft (370) and position the sampling head (320) of the swab in the approximate center of the shield (300). This prevents the sample present on the sampling head from contacting the shield. FIG. 3D is a transparent view of FIG. 3C. In FIG. 3D, the position of the sampling head (320) and shaft (330) of the swab may be seen within the shield (300).

In FIG. 4, FIG. 3C is shown rotated 90° C., along the lines R—R indicated in FIG. 3C. Thus, FIG. 4 provides a view of the shield (300) of FIG. 3C, which shows the large open end of the shield (i.e., the distal end of the shield), and the rim of the shield (350), with the swab positioned so that the sampling head (320) is in the approximate center of the shield (300).

It is not intended that the present invention be limited to particular shield or swab dimensions. Rather, the present invention may be modified in any manner that allows a sample present on the sampling head of a swab to be protected within a shield, while preventing the touching of the sample to the inner aspect of the shield and facilitating the drying of the sample.

It is clear that the present invention provides devices and methods for the collection and transport of forensic samples that avoid the problems encountered with other methods. In particular, it is clear that the present invention provides a method for the efficient and protected drying of samples present on swabs.

What is claimed is:

1. A sample collection and transport device, comprising:
    a) a sample collection means including a shaft having distal and proximal ends and a sampling head mounted on said proximal end of said shaft; and
    b) a perforated shield having a collar for slidingly engaging said shaft of said sample collection means, said perforated shield having a shape and size sufficiently large to surround said sampling head without substantially touching said sampling head when said sampling head is drawn into said perforated shield.

2. The sample collection and transport device of claim 1, wherein said sampling head of said collection means is an absorbent.

3. The sample collection and transport device of claim 1, wherein said shield is composed substantially of rigid plastic.

4. The sample collection and transport device of claim 1, wherein said collar is a guiding hub.

* * * * *

UNITED STATES PATENT AND TRADEMARK OFFICE
CERTIFICATE OF CORRECTION

PATENT NO. : 5,874,045
DATED : 02/23/99
INVENTOR(S) : William J. Chisum

It is certified that error appears in the above-identified patent and that said Letters Patent is hereby corrected as shown below:

In column 4, line 23, please delete "FIGS. 1A-E" and insert -- FIGS. 1A-1E --.
In column 4, line 23, please delete "FIGS. 2A-C" and insert -- FIGS. 2A-2C --.
In column 4, line 29, please delete "FIGS. 3A-D" and insert -- FIGS. 3A-3D --.
In column 4, line 35, please delete "FIGS. 5A-D" and insert -- FIGS. 5A-5D --.
In column 7, line 15, after "FIG 5A-5D", please insert -- are a --.

Signed and Sealed this

Fourth Day of April, 2000

Q. TODD DICKINSON

*Attest:*

*Attesting Officer*      *Director of Patents and Trademarks*